United States Patent [19]

Korthuis et al.

[11] Patent Number: 5,700,830
[45] Date of Patent: Dec. 23, 1997

[54] USE OF NITRIC OXIDE-RELEASING AGENTS FOR REDUCING METASTASIS RISK

[75] Inventors: Ronald J. Korthuis; Lipu Kong, both of Shreveport, La.; Larry K. Keefer, Bethesda, Md.

[73] Assignee: The United States of America as represented by the Department of Health and Human Services, Washington, D.C.

[21] Appl. No.: 344,341

[22] Filed: Nov. 22, 1994

[51] Int. Cl.$^6$ .............. A61K 31/40; A61K 31/535; A61K 31/445; A61K 31/495; A61K 31/13
[52] U.S. Cl. .............. 514/426; 514/231.2; 514/315; 514/255; 514/611
[58] Field of Search .................. 514/426, 231.2, 514/315, 255, 611

[56] References Cited

U.S. PATENT DOCUMENTS 5,212,204  5/1993  Keefer et al. .................. 514/647
5,250,550  10/1993 Keefer et al. .................. 514/357

FOREIGN PATENT DOCUMENTS

WO 93/07114  4/1993  WIPO.
WO 93/20806  10/1993 WIPO.

*Primary Examiner*—Jerome D. Goldberg
*Attorney, Agent, or Firm*—Leydig, Voit, & Mayer, Ltd.

[57] ABSTRACT

A method for inhibiting the adherence between cancerous cells and noncancerous structures in a mammal, comprising the administration to the mammal of a nitric oxide-releasing compound containing a nitric oxide-releasing $N_2O_2^-$ functional group. The compound is capable of releasing an adherence-inhibiting effective amount of nitric oxide to the mammal.

4 Claims, 1 Drawing Sheet

USE OF NITRIC OXIDE-RELEASING AGENTS FOR REDUCING METASTASIS RISK

TECHNICAL FIELD OF THE INVENTION

The present invention relates to a method of inhibiting the adherence between cancerous and non-cancerous cells in a mammal, and, more particularly, to reduce metastasis risk in a mammal using a nitric oxide-releasing agent containing a nitric oxide-releasing $N_2O_2^-$ functional group.

BACKGROUND OF THE INVENTION

Current methods of treating cancer include surgery, radiotherapy, chemotherapy and immunotherapy. Usually, one or more of these methods is used in combination, with surgery and radiotherapy being the most eradicative. However, given that surgery and radiotherapy are both local treatment methods, these treatments are only useful when tumors are localized. If the cancer is systemic or metastatic, chemotherapy and immunotherapy are more useful treatment methods.

Metastasis is one of the most serious problems of tumor therapy, causing most of the fatal conditions. The risk of metastasis is especially high during the treatment of primary tumors so that there is an urgent need for preventing the formation of metastases at this stage.

Metastasis involves the release of cancerous cells from a primary tumor into the circulatory or lymphatic system followed by adhesion of the cancerous cells to the walls of capillaries and postcapillary venules and extravasation, resulting in the migration of the cancerous cells to a new tissue site and formation of one or more secondary tumors. Once the tumor cells gain access to the circulation, subsequent steps in the metastatic cascade involve the adhesion to microvessel endothelium and invasion of the basement membrane, the thin extracellular matrix that surrounds the blood vessel wall and which is believed to be degraded by specific proteolytic enzymes. The adhesion of the metastasizing cancerous cells to the endothelium is mediated by adhesive structures, such as VCAM, VLA-4, E-selectin and sialyl-Lewis X. Similarly, the adhesion of tumor cells to the basement membrane is mediated through specific cell-surface receptors that bind to various glycoproteins, such as laminin, fibronectin and chondronectin.

Laminin is a basement membrane-specific glycoprotein composed of three chains, namely α, β1, and β2, which form a cruciform shape, and is the glycoprotein preferred by a number of carcinomas, e.g., of colon and breast (Liotta, *Cancer Res.*, 46, 1–7 (1986); Terranova et al., *PNAS USA*, 80, 444–448 (1983); Terranova et al., *Cancer Res.*, 42, 2265–2269 (1982); and Vlodavsky et al., *Nature*, 289, 304–306 (1981)). Laminin is active in promoting cell adhesion, migration, proliferation, neurite outgrowth and differentiation (See, e.g., Timpl et al., *J. Biol. Chem.*, 254, 993 (1979), Engel et al., *J. Mol. Biol.*, 150, 97 (1981), Kleinman et al., *J. Cell. Biochem.*, 27, 317 (1985), and Graf et al., *Cell*, 48, 989 (1987)). Malignant cells, which have laminin receptors on their surfaces, bind and attach more readily to laminin than normal cells.

Motility factors and tissue chemotactic factors can stimulate the movement of malignant tumor cells and have been implicated in the organ-specific metastasis of certain tumor cells (Hujanen et al., *Cancer Research*, 45, 3517–3521 (1985)). Chemoattractants may have a significant role in tumor cell metastasis.

Given that metastasis involves the spread of tumor cells to organ sites distant from the primary tumor, various forms of chemotherapy and immunotherapy have been used in the treatment of metastasis. Conventional chemotherapy has been predominantly carried out using inhibitors of nucleic acid or protein synthesis, such as 5-fluorouracil (5FU), mitomycin (MMC), cisplatin (CDDP) or adriamycin (ADR). However, these inhibitors are accompanied by such pronounced side effects that their use essentially has been restricted to auxiliary treatment.

Recently, an attempt has been made to treat cancer by enhancing the foreign body exclusion mechanism, an immunological defense system, through the administration of cytokines, such as interferons and interleukins. Naturally, however, these substances are locally produced only when a foreign body has invaded an organism. Consequently, general or systemic administration of such compounds also results in side effects. Furthermore, given that cancer cells are recognized as foreign bodies by an organism only with difficulty, the cancer to which the treatment can be applied is very limited. Similarly, the use of immunopotentiating antitumor agents, such as biological response modifiers (BRM), also is accompanied by side effects.

U.S. Pat. Nos. 5,306,714 (Okamoto et al., Apr. 26, 1994) and 5,004,735 (Okamoto et al., Apr. 2, 1991) disclose the use of (S)-2,3-dihydropolyprenol and (S)-2,3-dihydropolyprenol monophosphate and pharmaceutically acceptable salts thereof in the treatment of metastasis.

Lactams, such as N-(3-phenylpropyl)-1-deoxynojirimycin, 1-deoxynojirimycin, D-glucaro-δ-lactam, and 6-O-triphenylmethyl-D-gluco-δ-lactam, are described in U.S. Pat. No. 4,985,445 (Suzuki, Jan. 15, 1991) as inhibitors of metastasis.

U.S. Pat. No. 5,242,692 (Djaldetti et al., Sep. 7, 1993) discloses a tumor cell proliferation inhibitor with a molecular weight of about 25,000–30,000 daltons that is isolatable from muscle tissue and muscle cell culture.

U.S. Pat. No. 5,231,082 (Schasteen, Jul. 27, 1993) discloses antimetastatic cyclic peptides. The cyclic peptides are said to bind to the 67 kDa laminin receptor and to block laminin-mediated cell adhesion and colonization by melanoma cells. Other antimetastatic peptides, which include the pentapeptide tyr-ile-gly-ser-arg, are disclosed in European Patent Application Publication No. 0278781, Iwamoto et al., *Science*, 238, 1132 (1987), and Graf et al., *Biochemistry*, 26, 6896 (1987). A laminin β1 peptide and its use in the treatment of tumor cell metastasis is described in U.S. Pat. No. 5,175,251 (Johnson et al., Dec. 29, 1992). The administration of acylated peptides, such as pentapeptides, to inhibit metastasis is described in U.S. Pat. No. 5,039,662 (Schasteen, Aug. 13, 1991). Acylaminoalkylpyridineamide administration is described in U.S. Pat. No. 5,030,642 (Fuller et al., Jul. 9, 1991) as a method of treating metastasis. The amides are described as specific inhibitors of 5-lipoxygenase and are said to inhibit cell invasive activity and metastasis.

The use of 5-(2-chlorobenzyl)-4,5,6,7-tetrahydrothieno[3,2-c]pyridine to treat metastasis is described in U.S. Pat. No. 4,963,559 (Suzuki, Oct. 16, 1990).

Inhibition of metastasis through the administration of certain castanospermine esters and castanospermine is described in U.S. Pat. Nos. 4,952,585 (Sunkara et al., Aug. 28, 1990) and 4,792,558, respectively.

The use of monosaccharides that are specific for organ cell lectins and/or glycoconjugates containing such monosaccharides, specifically β-D-galactose and/or glycoconjugates containing terminal β-D-galactose moieties, to treat metastasis is described in U.S. Pat. No. 4,946,830 (Pulverer et al., Aug. 7, 1990).

Terranova et al. ((1982), supra), discloses treating certain metastatic cells with an antibody to laminin, which decreases the ability of the metastatic cells to interact with basement membrane and reduces the number of metastases produced when the cells are injected into mice.

Administration of a ribonuclease inhibitor to control metastasis, such as that which occurs from primary tumors in the lung, breast and colon, is described in U.S. Pat. No. 5,175,005 (Fukushima et al., Dec. 29, 1992).

The use of compounds that inhibit protein kinase-C as a means of inhibiting metastasis is disclosed in U.S. Pat. No. 5,151,360 (Handa et al., Sep. 29, 1992).

The use of N,N,N-trimethylsphingosine to inhibit metastasis is described in U.S. Pat. No. 5,137,919 (Igarashi et al., Aug. 11, 1992).

The administration of lipids obtained from black currant seed, in the form of a dietetic or pharmaceutical composition, which promotes the bioavailabity of eicosapentanoic acid and dihomogammalinolenic acid, while depressing the bioavailability of arachinoic acid, to prevent cell adhesion and, therefore, metastasis is described in U.S. Pat. No. 5,141,958 (Crozier-Willi et al., Aug. 25, 1992).

The administration of the lectins Abrin and Abrus agglutinin to suppress post-surgical malignant tumor metastasis is disclosed in U.S. Pat. No. 5,053,386 (Tung, Oct. 1, 1991). The administration of a 5-amino- or substituted amino-1,2,3-triazole after surgical excision of tumors characterized by a high probability of metastasis, such as melanoma and breast cancer, is described in U.S. Pat. No. 5,045,543 (Hupe, Sep. 3, 1991).

Accordingly, it is evident that there are many tumor-inhibiting substances in actual use and many more substances described as having potential use in the treatment of cancer, generally, and, more specifically, in the treatment of metastasis. However, even today there is no general cure for cancer and, therefore, any contribution to chemotherapy is welcomed by the medical profession in hopes of obtaining, at the very least, a more effective agent in the treatment of cancer and associated metastases.

Tumor cells that synthesize NO appear to be less metastatic than those that do not (Radomski et al., Cancer Research, 51, 6073–6078 (1991); Dong et al., Cancer Research, 54, 789–7793 (1994)). Whether or not the administration of exogenous NO has an effect on metastasis is not known. However, the problem with testing this hypothesis by using commercially available NO-releasing compounds is these compounds' inability to release NO site-specifically. It would be undesirable to treat cancer patients with NO prodrugs currently on the market that release NO throughout the body because this would produce unwanted side effects in other NO-sensitive tissues that could override any beneficial effects on the tumor cells.

Nitric oxide in its pure form is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

A number of compounds have been developed which are capable of delivering nitric oxide for pharmacological purposes, including compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)), which are relatively stable but release nitric oxide on activation. While this feature may be an advantage in some applications, it also can be a significant liability. For example, tolerance to glyceryl trinitrate can develop via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14 (Suppl. 11), S47–S54 (1989)). Also, prolonged administration of nitroprusside results in the metabolic production of cyanide, which leads to toxicity (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

A very important class of NO-releasing agents is the nitric oxide-nucleophile complexes, compounds containing the NO-releasing $N_2O_2^-$ ("NONOate") functional group. Numerous nitric oxide-nucleophile complexes have been described, e.g., Drago, *ACS Adv. Chem. Ser.*, 36, 143–149 (1962). See also Longhi and Drago, *Inorg. Chem.*, 2, 85 (1963). Many of these complexes are known to evolve nitric oxide on heating or hydrolysis, e.g., Maragos et al., *J. Med. Chem.*, 34, 3242–3247 (1991).

Recently, a method for treating cardiovascular disorders in a mammal with certain nitric oxide-nucleophile complexes was disclosed, e.g., in U.S. Pat. No. 4,954,526. These compounds contain the anionic $N_2O_2^-$ group or derivatives thereof. See also, Maragos et al., supra. Many of these compounds have proven especially promising pharmacologically because, unlike nitrovasodilators such as nitroprusside and nitroglycerin, they release nitric oxide without first having to be activated. The only other series of drugs currently known to be capable of releasing nitric oxide purely spontaneously is the S-nitrosothiol series, compounds of structure R—S—NO (Stamler et al., *Proc. Natl. Acad. Sci. U.S.A.*, 89, 444–448 (1992)); S-nitroso-N-acetylpenicillamine has been reported to release nitric oxide in solution and to be effective at inhibiting DNA synthesis (Garg et al., *Biochem. and Biophys. Res. Comm.*, 171, 474–479 (1990)). However, the R—S—NO→NO reaction is kinetically complicated and difficult to control (Morley et al., *J. Cardiovasc. Pharmacol.*, 21, 670–676 (1993)). Similarly, compounds like molsidomine and linsidomine not only require activation to release NO, but they also release undesirable free radicals. The NONOates, therefore, are thus advantageous among currently known drugs in that they decompose at any given pH by a first-order reaction to provide doses of nitric oxide that can be predicted, quantified, and controlled. See, e.g., Maragos et al., supra.

Nitric oxide/nucleophile complexes which release nitric oxide in aqueous solution are also disclosed in U.S. Pat. Nos. 5,039,705, 5,155,137, 5,185,376, 5,208,233, 5,212,204, 5,250,550, as well as in pending U.S. patent application Ser. Nos. 07/950,637 (filed Sep. 23, 1992), and 07/858,885 (filed Mar. 27, 1992), as being useful cardiovascular agents (see also Maragos et al., *J. Med. Chem.*, 34, 3242–3247 (1991)).

Despite considerable investigation and the expenditure of substantial resources, there still remains a need for effective treatment of cancer. More particularly, there remains a need for an effective method of inhibiting adherence between cancerous cells and noncancerous structures, such as that which occurs in metastasis. Thus, in one aspect, the present invention provides a method for the inhibition of adherence between cancerous cells and noncancerous structures, such as that which occurs in metastasis, in a patient in need thereof. Other objects and advantages of the present invention, as well as additional inventive features, will be apparent from the description of the invention provided herein.

SUMMARY OF THE INVENTION

The present invention provides a method for inhibiting the adherence between cancerous cells and noncancerous structures in a mammal, in particular a human. The method comprises the administration to a mammal in need thereof a nitric oxide-releasing agent containing the nitric oxide-releasing functional group $N_2O_2^-$. The nitric oxide-releasing agent releases an adherence-inhibiting effective amount of nitric oxide to the mammal to inhibit adherence between cancerous cells and noncancerous structures, wherein the term "noncancerous structures" refers to cells, tissues, membranes, organs and the like. The present invention provides a method for reducing the risk of metastasis which also comprises the administration of a nitric oxide-releasing agent to a mammal in need thereof.

The agent may be a monomer containing a nitric-oxide releasing $N_2O_2^-$ functional group or it may be a polymeric composition comprising a polymer to which is bound a nitric oxide-releasing $N_2O_2^-$ functional group. The polymer can also be a biopolymer. The agent is capable of locally releasing an adherence-inhibiting effective amount of nitric oxide to a site at risk for adherence between cancerous cells and noncancerous structures in said mammal, and especially to a site at risk for metastasis.

DETAILED DESCRIPTION OF THE INVENTION

Figure 1:
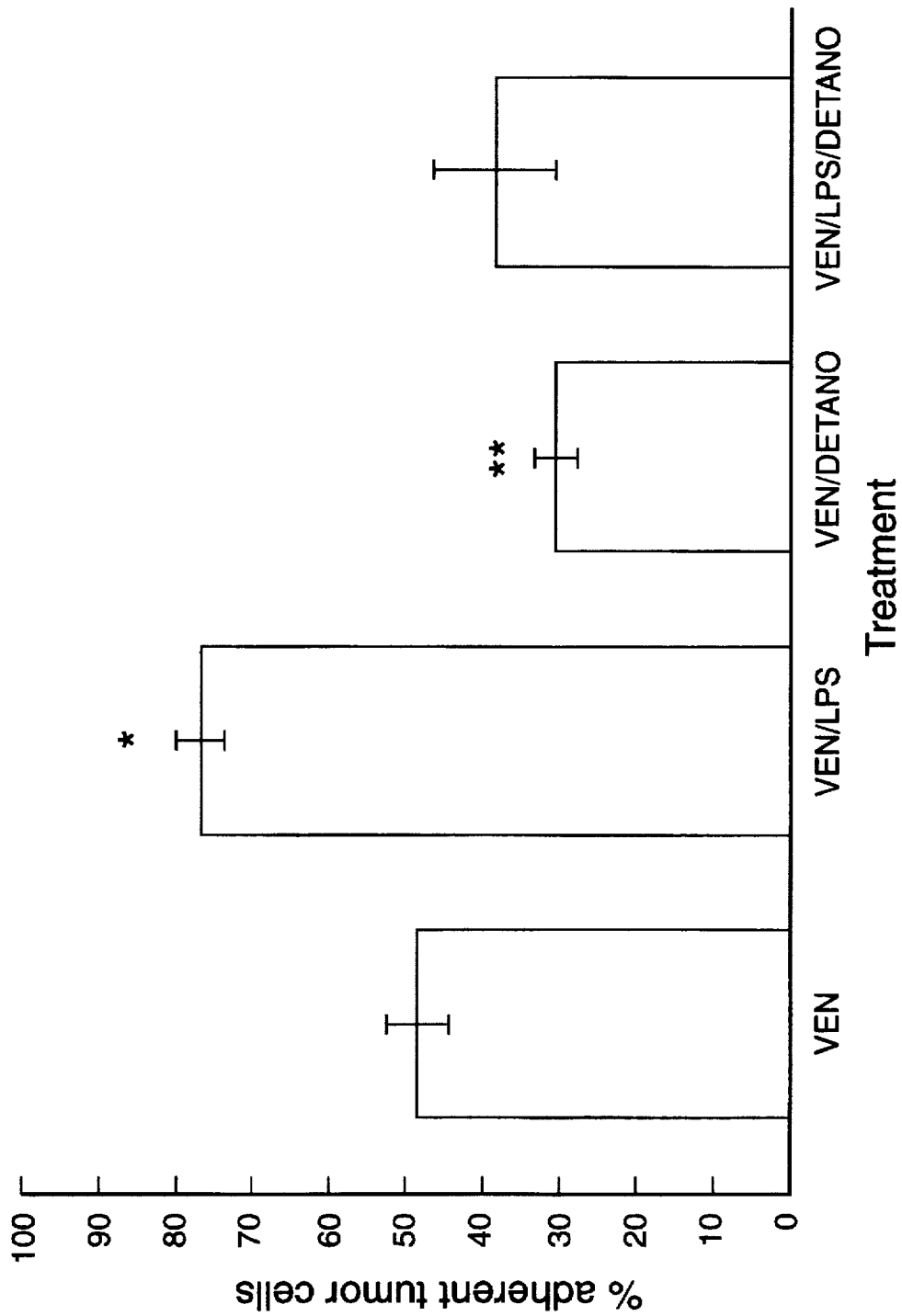
FIG. 1 is a bar graph of % adherent tumor cells versus venules (VEN) and arterioles (ART) in the absence or presence of lipopolysaccharide (LPS), DETA/NO ($H_2NCH_2CH_2N[N(O)NO]^-CH_2CH_2NH_3^+$), or LPS and DETA/NO.

The present invention provides a method for inhibiting the adherence between cancerous cells and noncancerous structures in a mammal, and is useful for reducing the risk of metastasis in a mammal. The method involves the administration to a mammal, in particular a human, of a nitric oxide-releasing agent which contains the nitric oxide-releasing functional group $N_2O_2^-$. The agent is a compound comprising a nitric oxide-releasing $N_2O_2^-$ functional group or a polymeric composition comprising a polymer to which is bound a nitric oxide-releasing $N_2O_2^-$ functional group. The agent is capable of attaching (e.g., via immunochemical interaction) to potentially metastatic cancerous cells, thereby dosing them with enough NO to inhibit metastasis, or of locally releasing an adherence-inhibiting effective amount of nitric oxide at a site of a noncancerous structure at risk for metastasis in the mammal. The nitric oxide-releasing polymeric composition may be administered in many forms, such as an organ- or cell-specific biopolymer or as an implant, liposome, microparticle, microsphere, bead, or disk as described more fully below. "Adherence-inhibiting effective" amount is as described below with respect to dosages.

Useful pharmacological agents can be provided by incorporating nitric oxide-releasing $N_2O_2^-$ functional groups into a monomer or polymer, including a biopolymer. The nitric oxide-releasing agents suitable for use in the method of the present invention are defined by the formula:

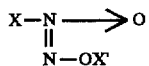

wherein X is an organic or inorganic moiety and X' is an organic or inorganic substituent, a pharmaceutically acceptable metal center, a pharmaceutically acceptable cation, or the like. The $N_2O_2^-$ group is bonded to the biopolymer through either or both the linking groups X and X'.

The nitric oxide-releasing $N_2O_2^-$ functional group is preferably a nitric oxide/nucleophile adduct, i.e., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, X=2-(ethylamino)ethylamine, as in the zwitterion $CH_3CH_2N[N(O)NO]^-CH_2CH_2NH_3^+$, or X=3-(n-propylamino)propylamine, as in the zwitterion $CH_3CH_2CH_2N[N(O)NO]^-CH_2CH_2CH_2NH_3^+$, or oxide (i.e., $X=O^-$, as in $NaO[N(O)NO]Na$), or a derivative thereof. Such nitric oxide/nucleophile complexes are capable of delivering nitric oxide in a biologically usable form at a predictable rate.

Suitable nitric oxide/nucleophile complexes include those having the following formula:

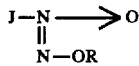

wherein J is an organic or inorganic moiety, including, for example, a moiety which is not linked to the nitrogen of the $N_2O_2^-$ group through a carbon atom, $M^{+x}$ is a pharmaceutically acceptable cation, where x is the valence of the cation, a is an integer of at least one, and b and c are the smallest integers that result in a neutral compound, as described in U.S. Pat. No. 5,212,204, incorporated herein by reference;

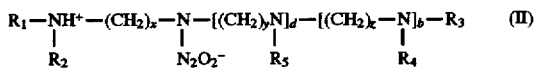

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137, incorporated herein by reference;

wherein B is

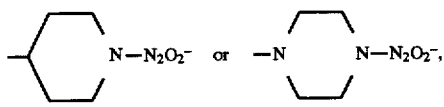

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

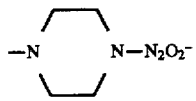

then f is an integer from 2 to 12, as described in U.S. Pat. No. 5,155,137, incorporated herein by reference;

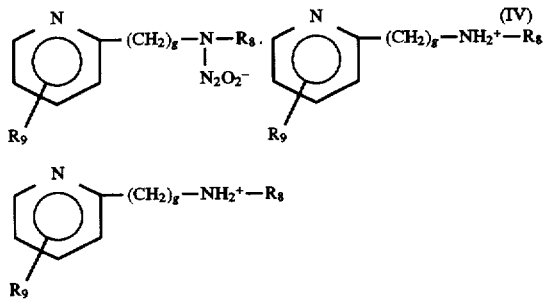

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is 2 to 6, as described in U.S. Pat. No. 5,250,550, incorporated herein by reference;

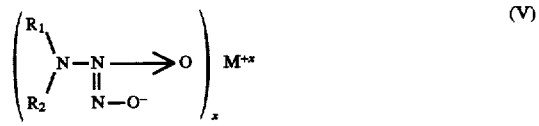

wherein $R_1$ and $R_2$ are independently selected from the group consisting of a straight chain or branched chain $C_1$–$C_{12}$ alkyl group and a benzyl group, or else $R_1$ and $R_2$, together with the nitrogen atom, are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. Nos. 5,039,705 and 5,208,233 and U.S. patent application Ser. No. 08/017,270, filed Feb. 12, 1993, and incorporated herein by reference;

wherein M is a pharmaceutically acceptable metal, or, where x is at least two, a mixture of two different pharmaceutically acceptable metals, L is a ligand different from ($R^1R^2N$—$N_2O_2$) and is bound to at least one metal, $R^1$ and $R^2$ are each organic moieties and may be the same or different, x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. patent application Ser. No. 07/858,885, filed Mar. 27, 1992, and incorporated herein by reference;

wherein R is $C_{2-8}$ lower alkyl, phenyl, benzyl, or $C_{3-8}$ cycloalkyl, any of which R groups may be substituted by one to three substituents, which are the same or different, selected from the group consisting of halo, hydroxy, $C_{1-8}$ alkoxy, —$NH_2$, —$C(O)NH_2$, —$CH(O)$, —$C(O)OH$, and —$NO_2$, X is a pharmaceutically acceptable cation, a pharmaceutically acceptable metal center, or a pharmaceutically acceptable organic group selected from the group consisting of $C_{1-8}$ lower alkyl, —$C(O)CH_3$, and —$C(O)NH_2$, and y is one to three, consistent with the valence of X, as described in U.S. Pat. No. 4,954,526 and incorporated herein by reference; and

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$, together with the nitrogen atom to which they are bonded, form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—$ON=N(O)NR_1R_2$, wherein n is an integer of 2–8, and $R_1$ and $R_2$ are as defined above; preferably $R_1$, $R_2$ and $R_3$ do not contain a halo or a hydroxy substituent α to a heteroatom, as described in U.S. patent application Ser. No. 07/950,637, filed Sep. 23, 1992.

In keeping with the invention, the nitric oxide-releasing agent may be a polymeric composition or biopolymeric compositions as described in Saavedra et al., U.S. application filed on even date herewith. The term "bound to the polymer" means that the $N_2O_2^-$ functional group is associated with, part of, incorporated with or contained within the polymer physically or chemically. Physical association or bonding of the $N_2O_2^-$ functional group to the polymer may be achieved by coprecipitation of the polymer with a nitric oxide/nucleophile complex as well as by covalent bonding of the $N_2O_2^-$ group to the polymer. Chemical bonding of the $N_2O_2^-$ functional group to the polymer may be by, for example, covalent bonding of the nucleophile moiety of the nitric oxide/nucleophile adduct to the polymer such that the nucleophile residue to which the $N_2O_2^-$ group is attached forms part of the polymer itself, i.e., is in the polymer backbone or is attached to pendant groups on the polymer backbone. The manner in which the nitric oxide-releasing $N_2O_2^-$ functional group is associated with, part of, incorporated with or contained within, i.e., "bound," to the polymer is inconsequential to the present invention and all means of association, incorporation and bonding are contemplated herein. It has been discovered that incorporation of the $N_2O_2^-$ functional group into a polymer provides a polymer-bound nitric oxide/nucleophile adduct composition that can be administered for localized release of NO to a biological site of interest. Site-specific delivery of the polymer-bound adduct composition enhances the selectivity of action of the nitric oxide-releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue, such as an antibody to fibrin or tissue thromboplastin. Similarly, attachment of $N_2O_2^-$ groups to peptides that mimic the recognition sequences of ligands for important receptors provides localized concentrated effect of nitric oxide release, as would attachment to oligonucleotides capable of site-specific interactions with target sequences in a nucleic acid. Other proteins, nucleic acids and polysaccharides, including hormones and motility, chemotactic and extravasating factors or agents, can be similarly utilized.

For example, a piperazine containing a protected $N_2O_2^-$ group can be covalently attached to a polypeptide comprising the IKVAV recognition sequence important in tumor cell chemotaxis. If the resulting molecule retains both the capacity to regenerate NO as an antichemotactic agent and the affinity of the IKVAV sequence for tumor cells and/or sites in the vascular and lymphatic systems where the tumor cells tend to attach and extravasate, metastasis can be reduced or even prevented.

Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, and polyvinylchloride, polyethylenimine or derivatives thereof, polyethers such as polyethyleneglycol and polysaccharides, polyesters such as poly(lactide/glycolide), polyamides such as nylon and polyurethanes. Any of a wide variety of biopolymers can be used in the context of the present invention. Biopolymers suitable for use include peptides, polypeptides, proteins, oligonucleotides, nucleic acids, e.g., RNA and DNA, glycoproteins, glycogen, and the like. Alternatively, a subunit of a biopolymer, such as a fatty acid, glucose, an amino acid, a succinate, a ribonucleotide, a ribonucleoside, a deoxyribonucleotide, and a deoxyribonucleoside, can be used. Illustrative examples include antibodies or fragments thereof; extracellular matrix proteins such as laminin, fibronectin, or their cell attachment-site peptide recognition sequences, such as RGDS, IKVAV, YIGSR, and the like; and growth factors, peptide hormones, and other polypeptides for which there are high-affinity cell surface receptor sites, such as EGF, TGFα, TGFβ and TNF. Such molecules, upon receptor binding, may be internalized into the target cells, thereby facilitating intracellular delivery of the NO donor moiety.

Preferably for the polymer-bound and biopolymer-bound NONOates, the $N_2O_2^-$ functional group is bonded to the polymer or biopolymer through either or both the linking group X or X'.

The polymer-bound nitric oxide-releasing compositions may be administered in a wide variety of forms. Any form of delivery should adequately protect the integrity of the nitric oxide prior to its release and should control the release of the nitric oxide at such a rate, in such an amount, and in such a location as to serve as an effective means of inhibiting adherence between cancerous and noncancerous cells, and even more desirably for inhibiting the risk of metastasis. For example, delivery means for local administration or administration for localized release include, but are not limited to, implants, patches, stents, liposomes, microparticles, microspheres, beads, powders, liquids, gels, monolithic resins, disks or other devices. The advantages of local administration or release include the ability to attain effective concentrations of drug at the target site more quickly, the use of a smaller dose, and the realization of fewer toxic side effects than occur on systemic administration and release. Delivery means for systemic administration for localized release include, but are not limited to, solutions, suspensions, emulsions, capsules, sachets, tablets, dermal (topical) patches, lozenges, aerosols, liposomes, microparticles, microspheres, beads, prodrugs, small peptides that mimic ligand recognition sequences, and sequence-specific oligonucleotides as described above.

The nitric oxide-releasing complexes having $N_2O_2^-$ functional groups, including the compounds described above, may be bound to a polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent. Monomers containing the $N_2O_2^-$ group also may be dissolved in molten polymer which, upon solidification when the temperature is lowered, contains a rather uniform distribution of $N_2O_2^-$ groups within the matrix.

Alternatively, nitric oxide-releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. Where the $N_2O_2^-$ functional group is a group pendant to the polymer backbone, the polymer contains, or is derivatized with, a suitable nucleophile residue capable of reacting with nitric oxide to form the $N_2O_2^-$ functionality. Reaction of the polymer which contains a suitable nucleophilic residue, or of the suitably derivatized polymer, with nitric oxide thus provides a polymer-bound nitric oxide-releasing $N_2O_2^-$ functional group.

By way of illustration, several general means are available for synthesizing a biopolymeric composition comprising a biopolymer to which is attached a NONOate functional group. As one example, an ion of structure $X-N_2O_2^-$ is reacted with an electrophilic agent (an $[X']^+$-donor) to generate a covalently bonded NONOate of formula $X-N(O)=NOX'$; this protected complex is then attached to the desired biopolymer via the nucleophile residue, X, or the electrophile residue, X'. Alternatively, a nucleophile residue that is already part of (or that can be attached to) the biopolymer can be reacted with NO under basic conditions to give a nitric oxide complex containing a $N_2O_2^-$ functional group. As a specific example, a simple amino acid bearing a secondary amino group can be reacted with nitric oxide to generate a compound in accordance with the present invention. Similarly, the NO functionality can be attached to a basic nitrogen in a peptide. Alternative means can be used to attach NONOate-containing molecules to thiol or activated carboxylic acid groups in a peptide, polypeptide or protein in accordance with the present invention.

Further, byway of illustration, the $N_2O_2^-$ functional group may be attached to a peptide such as arg-gly-asp (RGD), to prepare the molecule arg-gly-asp-[N(O)NO]$^-$. Preferably, the RGD tripeptide would be attached to the NONOate through a linking group such as additional peptide units. Other receptor/ligand recognition sequences may be used analogously.

One skilled in the art will appreciate that suitable methods of administering the nitric oxide-releasing compounds and the polymer-bound nitric oxide-releasing $N_2O_2^-$ functional group compositions of the present invention to an animal are available, and that, although more than one route can be used to administer a particular composition, a particular route can provide a more immediate and more effective reaction than another route. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The nitric oxide-releasing compositions of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular polymeric composition employed, the type of delivery means employed, the route of administration, the condition and weight of the animal to be treated, the timing of administration, and the length of time of administration. The size of the dose also will be determined by the existence, nature, and extent of any adverse side-effects that might accompany the administration of a particular composition. The dose may be administered acutely or chronically as dictated by the condition being treated, alleviated or prevented. An "adherence-inhibiting effective amount" of NO is an amount that inhibits adherence between cancerous cells and noncancerous structures as defined above.

The following examples further illustrate the present invention, but do not limit the scope thereof.

EXAMPLES

Example I

This example illustrates the preparation of 1-(2S-carboxypyrrolidin-1-yl)-1-oxo-2-hydroxydiazene, disodium salt, as shown schematically as follows:

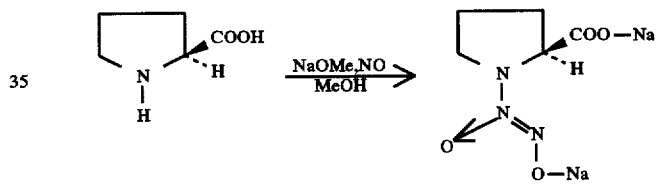

A solution of 10 g (0.087 mol) of L-proline in 39 ml (0.18 mol) of 25% sodium methoxide in methanol and 20 ml of methanol was degassed and exposed to 40 psi of NO for 20 h. The pressure was released and the solid residue was collected by filtration, washed with ether, and dried under vacuum to give 17 g of a white solid: UV (0.01M NaOH) $\lambda_{max}$ ($\epsilon$) 250 nm ($\epsilon$=4.9 mM$^{-1}$ cm$^{-1}$); NMR (D$_2$O) $\delta$1.71 (m, 1H), 1.91 (m, 2H), 2.27 (m, 1H), 3.27–3.43 (m, 2H), 4.04 (m, 1H). A methanol peak was also present, but the solid was free of both proline and N-nitrosoproline.

Example II

This example illustrates the preparation of 1-hydroxy-2-oxo-3-carboxymethyl-3-methyl-1-triazene, disodium salt, as shown schematically as follows:

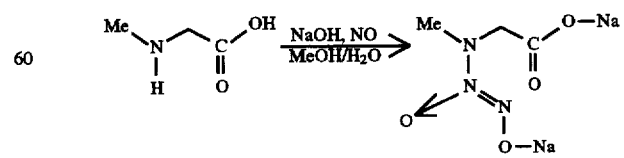

To a solution of 8 g (0.2 mol) of sodium hydroxide in 100 ml of methanol and 20 ml of water was added 8.9 g (0.1 mol)

of sarcosine. The solution was charged with 40 psi of NO and stirred at 25° C. for 48 h. The pressure was released, and the solution was evaporated in vacuo to give a white solid: UV $\lambda_{max}$ 250 nm. The distillate had a strong amine odor, which was determined to be methylamine on derivatization with benzoyl chloride.

The solid residue was dried under high vacuum, then analyzed by NMR in $D_2O$. Five products were detected by NMR: methylamine, δ2.28, 36%; 1-dimethylamino-1-oxo-2-hydroxydiazene, sodium salt, δ2.79, 15%; N-nitrosodimethylamine, δ3.11 and 3.91, 8%; N-nitrososarcosine, sodium salt, δ3.15 (s, E methyl), 3.84 (s, Z methyl), 4.21 (s, Z methylene), 4.80 (s, E methylene), 10%. The title compound was present as 32% of the mixture: δ3.11 (s, 3H) and 3.60 (s, 2H).

Example III

This example illustrates the preparation of 1-hydroxy-2-oxo-3-carboxymethyl-3-methyl-1-triazene N-methylamide, sodium salt, as shown schematically as follows:

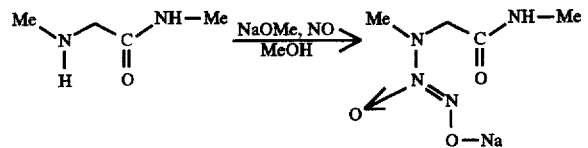

A solution of 150 ml (1.9 mol) of 40% aqueous methylamine was cooled to 0° C. To the solution was added 40 ml of 10M sodium hydroxide followed by the careful addition over a 2-h period at 0° C. of α-chloroacetyl chloride (27 g, 0.24 mol).

Stirring was continued at room temperature overnight. The resulting solution was saturated with sodium chloride and extracted with dichloromethane, dried over sodium sulfate, and filtered through a layer of magnesium sulfate. Most of the solvent was removed on a rotary evaporator and the residue was distilled at 1 atm then under moderate vacuum. The product distilled at 90°-2° C. at 125 mm Hg to yield 15 g (61%) of sarcosine N-methylamide: IR (film) 3318, 2952, 2889, 1659, 1553, 1462, 1413, 1166 $cm^{-1}$; NMR ($CDCl_3$) δ2.42 (s, 3H), 2.86 (s, 1.5H), 2.83 (s, 1.5H), 3.23 (s, 2H).

A solution of 1.7 g (0.0167 mol) of sarcosine N-methylamide in 3.5 ml (0.016 mol) of 25% sodium methoxide in methanol was placed in a pressure bottle, flushed with nitrogen and charged with 40 psi of nitric oxide. The solution was kept at 25° C. for 48 h, giving a thick paste. The pressure was released. The residue was washed with ether and dried under vacuum to give 1.4 g of a solid: UV $\lambda_{max}$ (ε) 250 nm (2.4 $mM^{-1}$ $cm^{-1}$).

Example IV

This example illustrates the preparation of the bis(nitric oxide) adduct of L-prolyl-L-leucylglycinamide, as shown schematically as follows:

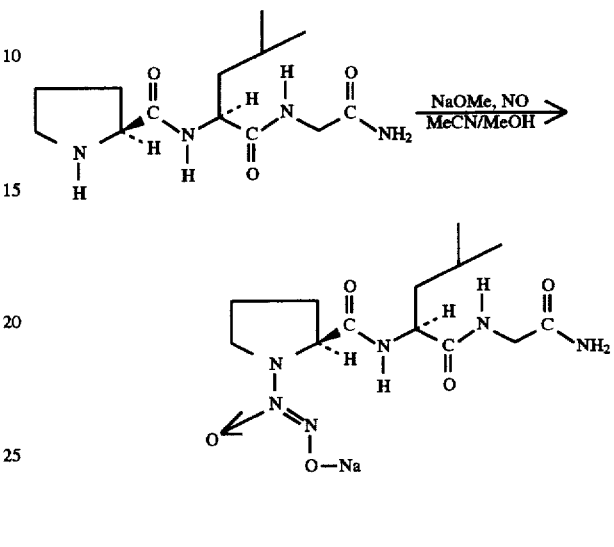

To a slurry of 120 mg (0.423 mmol) of L-prolyl-L-leucylglycinamide (Sigma) in 4 ml of acetonitrile was added 100 μl of 25% sodium methoxide in methanol. The resulting gel was treated with a few drops of methanol until a homogeneous solution was obtained. The solution was transferred into a micro-Parr bottle and bubbled with nitrogen for 5 min, followed by exposure to 40 psi of NO for 72 h. The reaction mixture was dried under vacuum to give 187 mg of a solid: $\lambda_{max}$ (ε) 250 nm (6.2 $mM^{-1}$ $cm^{-1}$) in pH 7.4 buffer. It released 0.86 moles of NO (per mole of tripeptide decomposed at this pH) with a half-life of 7 min at 37° C.

Oligopeptides and proteins of increasing chain length can be similarly derivatized with NO.

Example V

This example demonstrates the attachment of a nucleophilic center to a protein that does not contain a nucleophilic center that will readily react with NO, shown schematically as follows:

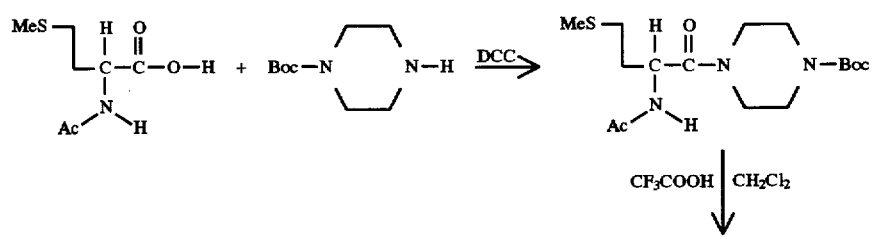

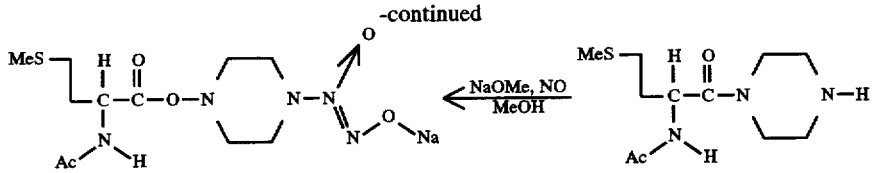

A solution of 4.78 g (0.025 mol) of N-acetyl-L-methionine in CH$_2$Cl$_2$: acetonitrile (120 ml) was cooled to 0° C. To this solution was added 5.36 g (0.025 mol) of dicyclohexylcarbodiimide (DCC) followed by the rapid addition of 3.90 g (0.021 mol) of N-t-butoxycarbonylpiperazine in 6 ml of dichloromethane. The progress of the reaction was followed on silica gel TLC plates developed with 4:1 acetonitrile: tetrahydrofuran and visualized with either iodine or ninhydrin spray. The reaction was complete within 2 h. A few drops of glacial acetic acid were added to the reaction mixture and the solvent was removed on a rotary evaporator. The residue was taken up in ether and filtered. The clear filtrate was washed with dilute acid followed by dilute base. The organic layer was separated, dried over anhydrous sodium sulfate, filtered, and evaporated to give 8.2 g of 1-(t-butoxycarbonyl)-4-(N-acetyl-L-methionyl)piperazine, a colorless oil which required no further purification: IR (film) 3304, 3058, 2973, 2931, 2868, 1701, 1645, 1539, 1420, 1237, 1173 cm$^{-1}$; NMR (CDCl$_3$) δ1.47 (s, 9H), 1.80 (m, 2H), 2.02 (s, 3H), 2.10 (s, 3H), 2.46 (m, 2H), 3.53 (m, 8H), 5.10 (M, 1H), 6.35 (b, 0.5H), 6.43 (b, 0.5H).

To a solution of 8.6 g (0.024 mol) of 1-(t-butoxycarbonyl)-4-(N-acetyl-L-methionyl)piperazine in 60 ml of dichloromethane was added 10 ml of trifluoroacetic acid and the mixture was stirred at room temperature overnight. The solution was extracted with water and the resulting aqueous solution was made basic with sodium hydroxide. The product was extracted with dichloromethane, dried over sodium sulfate, and filtered. Evaporation of the solvent gave 2.1 g of 1-(N-acetyl-L-methionyl)piperazine, as an oil: IR (film) 3304, 3051, 2917, 2861, 1645, 1546, 1448, 1377 cm$^{-1}$; NMR (CDCl$_3$) δ1.95 (m, 2H), 2.02 (s, 3H), 2.10 (s, 3H), 2.54 (m, 2H), 2.98 (m, 4H), 3.74 (m, 4H), 5.10 (m, 1H), 6.40 (b, 0.5H), 6.48 (b, 0.5H).

To a solution of 510 mg (1.97 mmol) of 1-(N-acetyl-L-methionyl)piperazine in 1 ml of methanol was added 428 µl (1.97 mmol) of 25% sodium methoxide in methanol. The system was degassed and charged with 40 psi of nitric oxide. After exposure of the solution to NO for 120 h, the pressure was released and the solid product was collected by filtration, washed with ether, and dried to give 27 mg of 1-[4-(N-acetyl-L-methionyl)piperazin-1-yl]-1-oxo-2-hydroxydiazene, sodium salt, as a white solid: UV λ$_{max}$ (ε) 252 nm (12.0 mM$^{-1}$ cm$^{-1}$). The product decomposed with a half-life of 6.9 min at pH 7 and 25° C. to produce 1.72 moles of NO per mole of test agent.

Example VI

This example demonstrates the attachment of a preformed NONOate containing a nucleophilic nitrogen atom to the C-terminus of a peptide, polypeptide or protein as shown schematically as follows:

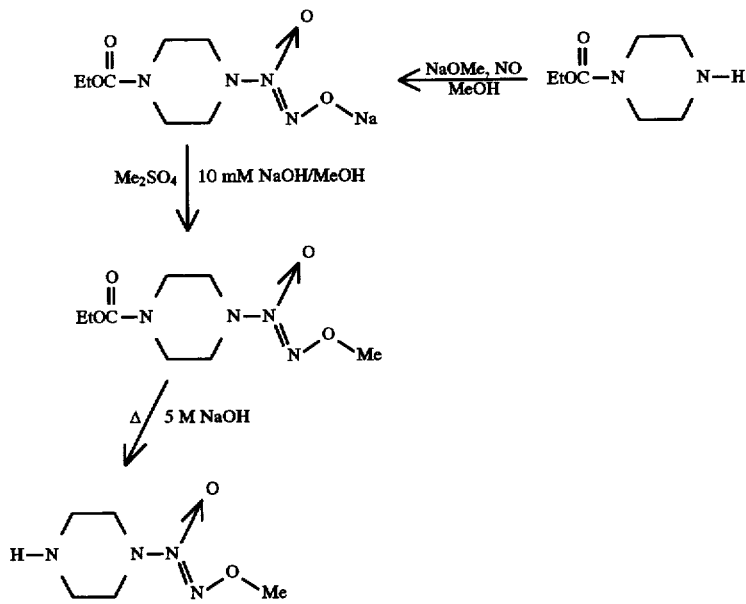

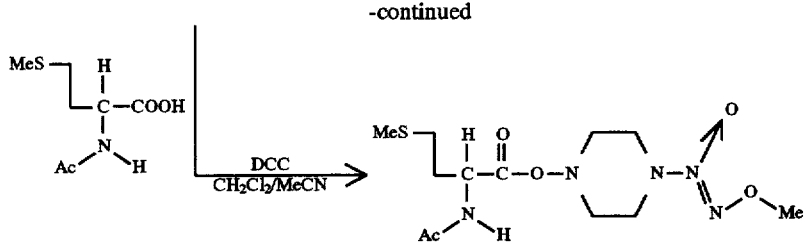

A solution of 20 g (0.126 mol) of ethyl 1-piperazinecarboxylate in 60 ml of methanol was placed in a Parr bottle. The solution was treated with 27.4 ml (0.126 mol) of 25% sodium methoxide in methanol. The system was evacuated, charged with 40 psi of nitric oxide and kept at 25° C. for 48 h. The white crystalline product was collected by filtration and washed with cold methanol as well as with copious amounts of ether. The product was dried under vacuum to give a 14.5 g (48%) yield of 1-(4-carbethoxypiperazin-1-yl)-1-oxo-2-hydroxydiazene, sodium salt: mp 184°–5° C.; UV (0.01M NaOH) $\lambda_{max}$ ($\epsilon$) 252 nm (10.4 mM$^{-1}$ cm$^{-1}$); NMR (D$_2$O) $\delta$1.25 (t, 3H), 3.11 (m, 2H), 3.68 (m, 2H), 4.15 (q, 2H). Anal Calcd. for C$_6$H$_{13}$N$_4$O$_4$Na: C, 35.00%; H, 5.42%; N, 23.33%; Na, 9.58%. Found: C, 34.87%; H, 5.53%; N, 23.26%; Na, 9.69%. The half-life of this compound at pH 7 and 25° C. was 5 min. This measurement was based on the loss of the 252-nm chromophore in the ultraviolet spectrum.

A solution of 1.3 g (5.4 mmol) of 1-(4-carbethoxypiperazin-1-yl)-1-oxo-2-hydroxydiazene, sodium salt, in 10 ml of 0.01M aqueous sodium hydroxide was cooled in an ice bath. A solution of 2 ml of dimethyl sulfate in 10 ml of methanol was added dropwise. The resulting solution was stirred at 0° C. for 1 h, then allowed to warm gradually to room temperature. After 24 h the solution was concentrated on a rotary evaporator. The residue was extracted with dichloromethane, dried over sodium sulfate, and filtered through a layer of magnesium sulfate. The solvent was evaporated under reduced pressure and the residue was chromatographed on silica gel. Elution with 2:1 dichloromethane:ethyl acetate provided 683 mg (55%) of 1-(4-carbethoxypiperazin-1-yl)-1-oxo-2-methoxydiazene as an oil, which crystallized on standing: mp 46° C.; UV $\lambda_{max}$ ($\epsilon$) 240 nm (8.4 mM$^{-1}$ cm$^{-1}$); IR (film) 2988, 2945, 2875, 1707, 1504, 1068 cm$^{-1}$; NMR $\delta$3.38 (m, 4H), 3.67 (m, 4H), 4.03 (s, 3H), 4.16 (q, 2H); MS m/z (relative intensity, %), 232 (M$^+$, 3), 217 (16), 187 (10), 157 (100), 142 (5), 98 (4), 85 (27), 70 (26), 56 (94), 54 (19); exact mass calcd for C$_8$H$_{16}$N$_4$O$_4$ (M$^+$) 232.1171, found 232.1172. Anal Calcd for C$_8$H$_{16}$N$_4$O$_4$: C, 41.38%; H, 6.90%; N, 24.14%. Found C, 41.23%; H, 6.82%; N, 24.05%.

A mixture of 1.8 g (0.0078 mol) of 1-(4-carbethoxypiperazin-1-yl)-1-oxo-2-methoxydiazene and 20 ml of 5M aqueous sodium hydroxide was heated at reflux. After 45 min no starting material remained in the mixture, as assessed from qualitative thin layer chromatography. The solution was allowed to cool to room temperature and evaporated to a viscous residue, which was extracted with ethyl acetate, dried over sodium sulfate, filtered, and evaporated. The product was chromatographed on silica gel and eluted with 1:1 dichloromethane:acetone giving 820 mg (66%) of 1-(piperazin-1-yl)-1-oxo-2-methoxydiazene as a pale yellow oil: UV $\lambda_{max}$ ($\epsilon$) 234 nm (7.0 mM$^{-1}$ cm$^{-1}$); NMR $\delta$3.03 (m, 4H), 3.38 (m, 4H), 4.06 (s, 3H); IR (film) 3318, 2945, 2854, 1447, 1364, 1286, 1230, 1046, 1004 cm$^{-1}$; MS m/z (relative intensity, %) 160 (M$^+$, 2), 145 (7), 143 (10), 115 (9), 85 (56), 58 (7), 56 (100); exact mass calcd for C$_5$H$_{12}$N$_4$O$_2$ (M$^+$) 160.0960, found 160.0966.

To a solution of 164 mg (0.856 mmol) of N-acetyl-L-methionine in 10 ml of 1:1 dichloromethane:acetonitrile was added 206 mg (1 mmol) of dicyclohexylcarbodiimide (DCC) followed by the rapid introduction of 137 mg (0.856 mmol) of 1-(piperazin-1-yl)-1-oxo-2-methoxydiazene in 3 ml of dichloromethane. The reaction mixture was stirred at 25° C. for 4 h. A few drops of glacial acetic acid were added to decompose excess DCC. The mixture was filtered and evaporated. The residue was extracted with ethyl acetate, which in turn was washed with dilute hydrochloric acid, followed by dilute aqueous sodium hydroxide. The organic layer was dried over sodium sulfate, filtered through a layer of magnesium sulfate, and evaporated in vacuo. Purification of 1-(4-[N-acetyl]-L-methionylpiperazin-1-yl)-1-oxo-2-methoxydiazene was accomplished on silica gel using 4:1 acetonitrile:tetrahydrofuran as the eluant: UV $\lambda_{max}$ ($\epsilon$) 230 nm (8.7 mM$^{-1}$ cm$^{-1}$); NMR $\delta$2.02 (s, 3H), 2.07 (m, 2H), 2.11 (s, 3H), 3.46 (m, 4H), 3.83 (m, 4H), 4.03 (s, 3H), 5.15 (m, 1H), 6.28 (b, 0.5H), 6.35 (b, 0.5H); IR 3297, 2931, 2847, 1645, 1546, 1497, 1441, 1223 cm$^{-1}$; MS m/z (relative intensity, %), 333 (M$^+$, 4), 318 (2), 304 (3), 303 (16), 288 (12), 260 (11), 259 (100), 258 (9), 214 (78), 184 (37), 183 (10), 174 (5), 146 (26), 142 (56), 141 (5), 104 (63), 61 (60); exact mass calcd for C$_{12}$H$_{23}$N$_5$O$_4$S (M$^+$) 333.1470, found 333.1471.

Example VII

This example demonstrates the effect of nitric oxide-releasing compounds on the adhesion of tumor cells to isolated arterioles and venules.

RPMI 1846, a melanotic melanoma of a Syrian hamster, was obtained from the American Type Culture Collection, Rockville, Md., and grown in McCoy's 5A medium (GIBCO, Grand Island, N.Y.) supplemented with 20% fetal bovine serum (GIBCO, Grand Island, N.Y.) at 37° C. in a humidified 5% CO$_2$ atmosphere. Once confluent, cells were harvested by brief trypsinization with 0.25% trypsin (GIBCO), neutralized with complete culture medium, centrifuged at 100×g for 5 minutes and resuspended at a concentration of 10$^6$ cells/ml in 1% albumin physiological salt solution (APSS), consisting of 145.0 mM NaCl, 4.7 mM KCl, 2.0 mM CaCl$_2$, 1.17 mM MgSO$_4$, 1.2 mM NaH$_2$PO$_4$, 5.0 mM glucose, 2.0 mM pyruvate, 0.02 mM EDTA, and 3.0 mM 3-(N-morpholino) propanesulfonic acid (MOPS) buffer and 1% fetal bovine serum, buffered to a pH of 7.4, and filtered through P8 filter paper (Fisher Scientific, Pittsburgh, Pa.). The viability of tumor cells was checked by trypan blue staining and only cell suspensions with a viability greater than 90% were used for experiments.

Male Sprague-Dawley rats weighing between 50 g and 150 g were injected intraperitoneally with 1 ml/100 g PSS or 1 ml/100 g PSS containing LPS (Sigma, St. Louis, Mo.) at 1 mg/ml. Four hours later, the rats were anesthetized with inactin (100 mg/kg intraperitoneally). A midline abdominal incision was produced, the superior mesenteric artery was isolated and cannulated, and 1 ml of warm porcine gelatin ink solution was injected into the mesenteric vasculature via the superior mesenteric artery catheter to visualize microvessels. The porcine gelatin ink solution was prepared by dissolving 0.36 g porcine skin gelatin (Sigma, St. Louis, Mo.) and 0.2 ml nondialized India ink in 10 ml warm APSS and filtering through P8 filter paper. At this concentration, the gelatin solution was liquid at room temperature and solidifies at temperatures below 20° C.

A segment of bowel and attached mesentery was excised and placed in a dissecting chamber containing ice-cold, pH 7.4 PSS (same as APSS but without added serum). An unbranched segment of arteriole or venule, 70–100 μm in diameter (OD) and 1.5–2.0 mm in length, was dissected free, transferred to an isolated vessel chamber (Halpern type), cannulated on both ends with glass micropipettes ~50 μm in diameter, secured with 11-0 sutures, and bathed in 37° C. PSS equilibrated with room air. The bath solution was in constant renewal at a rate of 2 ml/min. The vessel lumen was perfused with 37° C. APSS via a gravity-fed reservoir connected to the inflow catheter. After cannulation, the vessel chamber was placed on an inverted microscope. A television camera mounted on the microscope was used to project the image onto a television monitor and the images were recorded using a videocassette recorder. A video time/date generator projected the time, stopwatch function, and date onto the monitor. A video caliper was used to measure the diameter of the vessel.

After a 30-min stabilization period, the vessel was perfused with tumor cell suspension. Perfusate inflow was then interrupted and the tumor cells were allowed to settle onto the endothelium. The number of cells sitting on the microvessel was observed and recorded. Twenty minutes later, perfusate flow was resumed at a pressure gradient of 115 cm $H_2O$ between inflow and outflow micropipettes. Five minutes later, the number of tumor cells remaining adherent to the vessel wall was counted and recorded. The percentage of adherent cells was calculated by dividing the number of tumor cells remaining adherent to the vessel wall after flow was resumed for 5 minutes by the total number of cells setting on the vessel wall when flow was interrupted. One-way ANOVA and Student-Newman-Keuls tests were used to analyze the differences among groups, which were considered significant at $P<0.05$.

In order to determine the effect of LPS on tumor cell adhesion to precapillary arterioles and postcapillary venules, rats were injected intraperitoneally with LPS (Sigma) dissolved in PSS (1 mg/ml) at a dose of 1 mg/100 g body weight, while the control rats were injected intraperitoneally with PSS at 1 ml/100 g body weight. Four hours later, the animals were sacrificed and an arteriole or venule was isolated from mesentery for tumor cell adhesion analysis as described above. Tumor cells were much more adhesive to untreated venules than to untreated arterioles, the difference being about 5-fold. LPS treatment of postcapillary venules for 4 hours significantly increased tumor cell adhesion as compared to untreated venules. However, LPS treatment of precapillary arterioles did not affect tumor cell adhesion to these vessels.

The effect of nitric oxide, in the form of DETA/NO, on melanoma tumor cell adhesion to untreated and LPS-treated postcapillary venules is shown in FIG. 1, which is a bar graph of % adherent tumor cells versus VEN and ART in the absence or presence of LPS, DETA/NO, or LPS and DETA/NO. Treatment of isolated postcapillary venules with 1 mM DETA/NO for 30 min before reperfusing completely blocked the enhancing effect of LPS on tumor cell adhesion enhancement to postcapillary venules. Furthermore, DETA/NO decreased tumor cell adhesion to untreated venules. The difference was significant at $P<0.05$.

These results show that NO administered exogenously in the form of an NO donor containing an $N_2O_2^-$ group can inhibit tumor cell adhesion to LPS-activated endothelium and that exogenous NO can further reduce the baseline adhesion of tumor cells to naive venular endothelial cells.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method for inhibiting the adherence between cancerous and noncancerous cells in a mammal in need thereof, comprising the administration to said mammal of a nitric oxide-releasing compound containing a nitric oxide-releasing $N_2O_2^-$ functional group and having the formula:

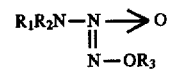

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{2-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—ON=N(O)$NR_1R_2$, wherein n is an integer of 2–8, and $R_1$ and $R_2$ are as defined above, said compound being capable of releasing an adherence-inhibiting effective amount of nitric oxide to said mammal.

2. The method of claim 1, wherein $R_1$ and $R_2$ together with the nitrogen atom to which they are bonded form a heterocyclic group selected from the group consisting of pyrrolidino, piperidino, piperazino, and morpholino.

3. The method of claim 1, wherein said cancerous cells in said mammal are potentially metastatic.

4. The method of claim 2, wherein the heterocyclic group is pyrrolidino and $R_3$ is vinyl.

* * * * *